United States Patent
Hu et al.

(10) Patent No.: US 11,660,501 B2
(45) Date of Patent: May 30, 2023

(54) SYSTEM FOR ANALYZING STARTS AND ACCELERATION PHASES IN SQUAT-STYLE TRACK AND FIELD EVENTS

(71) Applicant: National Formosa University, Huwei Township, Yunlin County (TW)

(72) Inventors: Nian-Ze Hu, Huwei Township, Yunlin County (TW); Li-Chun Yu, Huwei Township, Yunlin County (TW); Su-Hwa Ho, Huwei Township, Yunlin County (TW); Ching-Hua Li, Huwei Township, Yunlin County (TW)

(73) Assignee: NATIONAL FORMOSA UNIVERSITY, Huwei Township (TW)

( * ) Notice: Subject to any disclaimer, the term of this patent is extended or adjusted under 35 U.S.C. 154(b) by 440 days.

(21) Appl. No.: 17/090,417

(22) Filed: Nov. 5, 2020

(65) Prior Publication Data

US 2022/0134184 A1    May 5, 2022

(51) Int. Cl.
| | |
|---|---|
| A63B 24/00 | (2006.01) |
| G01C 19/00 | (2013.01) |
| G01L 5/00 | (2006.01) |
| A63K 3/02 | (2006.01) |
| A63B 69/00 | (2006.01) |
| G16H 20/30 | (2018.01) |

(Continued)

(52) U.S. Cl.
CPC ...... *A63B 24/0062* (2013.01); *A63B 24/0003* (2013.01); *A63B 69/0028* (2013.01); *A63K 3/023* (2013.01); *G01C 19/00* (2013.01); *G01L 5/00* (2013.01); *G01P 15/00* (2013.01); *G06N 20/00* (2019.01); *G06V 40/23* (2022.01); *G16H 20/30* (2018.01); *A63B 2220/807* (2013.01); *A63B 2220/836* (2013.01); *A63B 2225/50* (2013.01)

(58) Field of Classification Search
CPC ............ A63B 24/0062; A63B 24/0003; A63B 69/0028; A63B 2220/807; A63B 2220/836; A63B 2225/50; G16H 20/30; G06N 20/00; G06V 40/23; A63K 3/023; G01C 19/00; G01L 5/00; G01P 15/00
USPC ........................................................ 700/91
See application file for complete search history.

(56) References Cited

U.S. PATENT DOCUMENTS

| | | | |
|---|---|---|---|
| 10,032,069 B2 * | 7/2018 | Mizuochi | ............... G06V 40/23 |
| 2019/0240541 A1 * | 8/2019 | Denton | ............ A63B 21/00076 |

FOREIGN PATENT DOCUMENTS

| | | | |
|---|---|---|---|
| JP | 2018047252 A | * | 3/2018 |
| TW | 202009870 A | * | 3/2020 |

* cited by examiner

*Primary Examiner* — Allen Chan
(74) *Attorney, Agent, or Firm* — Birch, Stewart, Kolasch & Birch, LLP

(57) ABSTRACT

A system for analyzing starts and acceleration phases in squat-style track and field events has: a launching stand, a plurality of wireless cameras, a technical analysis host, two foot tracking devices and a gyro group. The launching stand has at least one acceleration sensor and an adjusting support connected to two pedals. The technical analysis host is connected to the acceleration sensor and the wireless cameras, the acceleration sensor actives the wireless cameras to collect instantaneous speed data of a runner, and the technical analysis host generates a 100 m speed curve L1 of the runner, and the 100 m speed curve L1 includes a continuous reduced acceleration section L2. The two foot tracking devices are installed on two feet of each runner. The gyro group have a first gyro, a second gyro, a third gyro and a fourth gyro.

9 Claims, 9 Drawing Sheets

(51) Int. Cl.
*G06N 20/00* (2019.01)
*G01P 15/00* (2006.01)
*G06V 40/20* (2022.01)

SYSTEM FOR ANALYZING STARTS AND ACCELERATION PHASES IN SQUAT-STYLE TRACK AND FIELD EVENTS

BACKGROUND OF INVENTION

Field of Invention

The present invention relates to a system for analyzing track and field events, and more particularly to a system for analyzing starts and acceleration phases in squat-style track and field events.

Description of Related Art

In order to achieve better performance, the runner needs to rely on the coach's experience guidance and the most ideal training mode. Also, a good starting mode has a high correlation with the acceleration period after the start, if the acceleration fails to rise as the ideal curve, it will cause an acceleration reduce period from the start stage to the acceleration stage after the start, and the acceleration reduce period lowers the average speed. If data analysis and data integration can be applied, each new runner can select a launching stand mode that is suitable during training, you, which can greatly shorten the time spent in the initial training. Furthermore, the acceleration reduce period during speed convergence is not only affected by the starting mode, but can also depends on the runner's physical conditions and the training status. Furthermore, the acceleration reduce period may occur at a certain moment between 30 m and 80 m on the track, which can only be discovered and effectively improved through the track and field data analysis system. However, the conventional track and field data analysis system with high cost of installation has led to the low popularity, and the conventional track and field data analysis system regards the runner's torso as a rigid body and only focuses on the front and rear tilt of the torso and the swing positions of the limbs. However, the tilt, twist and rotational deformation of the torso can increase the time-consuming movements of the limbs, also can cause unnecessary consumption of physical strength, and also can affect the running posture and the balance of the center of gravity. Moreover, ignoring the impact of the trunk on the track and field competition is equivalent to ignoring the core muscles of the torso, and the weak core muscles and the wrong way of exerting force both may cause the acceleration reduction period. Therefore, how to effectively find the time point of the acceleration reduction period and find the method of adjusting training are the issues need to be improved.

Therefore, it is desirable to provide a system for analyzing starts and acceleration phases in squat-style track and field events to mitigate and/or obviate the aforementioned problems.

SUMMARY OF INVENTION

An objective of present invention is to provide a system for analyzing starts and acceleration phases in squat-style track and field events, which is capable of improving the above-mention problems.

In order to achieve the above mentioned objective, A system for analyzing starts and acceleration phases in squat-style track and field events has: a launching stand, a plurality of wireless cameras, a technical analysis host, two foot tracking devices and a gyro group. The launching stand has at least one acceleration sensor and an adjusting support connected to two pedals. The technical analysis host is connected to the acceleration sensor and the wireless cameras, the acceleration sensor actives the wireless cameras to collect instantaneous speed data of a runner, and the technical analysis host generates a 100 m speed curve L1 of the runner, and the 100 m speed curve L1 includes a continuous reduced acceleration section L2. The two foot tracking devices are installed on two feet of each runner, each foot tracking device provides illumination for the wireless cameras to take a continuous left foot trajectory curve L3 and a continuous right foot trajectory curve L4. The gyro group have a first gyro, a second gyro, a third gyro and a fourth gyro.

Other objects, advantages, and novel features of invention will become more apparent from the following detailed description when taken in conjunction with the accompanying drawings.

DETAILED DESCRIPTION OF PREFERRED EMBODIMENT

Figure 1:
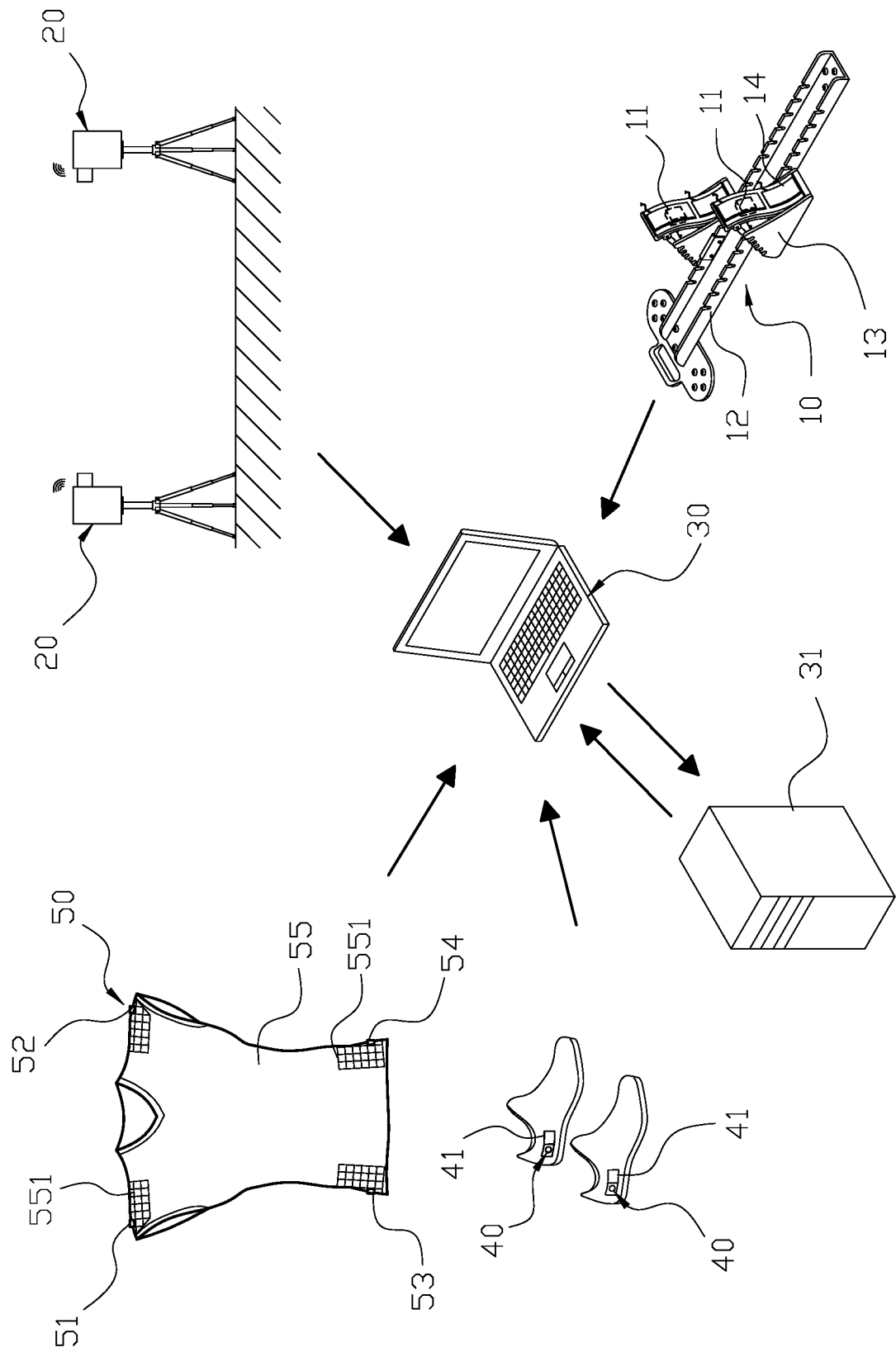
FIG. 1 is a schematic drawing of the system of a preferred embodiment according to the present invention.

Please refer to FIG. 1-FIG. 6. A system for analyzing starts and acceleration phases in squat-style track and field events comprises: a launching stand 10, a plurality of wireless cameras 20, a technical analysis host 30, two foot tracking devices 40 and a gyro group 50. The launching stand 10 has at least one acceleration sensor 11 and is disposed at a starting line (0 m) of a track, and an adjusting support 12 is connected to two pedals 13. Each pedal 13 is able to move along the adjusting support 12 and adjust to different angles, and the acceleration sensor 11 is installed behind the pedals 13. The plurality of wireless cameras 20 are cameras disposed on two sides of the track between 0 m to 100 m from the starting line and separated from each other by a predetermined distance, such as 10 m. The technical analysis host 30 is connected to the acceleration sensor 11 and the wireless cameras 20, the acceleration sensor 11 actives the wireless cameras 20 at launching to collect instantaneous speed data of a runner every 10 m, and the technical analysis host 30 generates a 100 m speed curve L1 of the runner, and the 100 m speed curve L1 includes a continuous reduced acceleration section L2 due to an acceleration phase of the starting action. The two foot tracking devices 40 are installed on two feet of each runner, each foot tracking device 40 provides illumination for the wireless cameras 20 to take a continuous left foot trajectory curve L3 and a continuous right foot trajectory curve L4. The gyro group 50 have a first gyro 51, a second gyro 52, a third gyro 53 and a fourth gyro 54. The first gyro 51 is mounted on a right shoulder of the runner, the second gyro 52 is mounted on a left shoulder of the runner, the third gyro 53 is mounted on a right waist of the runner, and the fourth gyro 54 is mounted on a left waist of the runner. Each gyro group 50 is connected to the technical analysis host 30 and measures relative running oscillations of each runner among an X axis, a Y axis, and a Z axis. Furthermore, the technical analysis host 30 determines whether to generate the continuous reduced acceleration section L2 of a runner according to the left foot trajectory curve L3 and the right foot trajectory curve L4 or according to relative oscillation of the body of the runner, so the training for the runner can be modified accordingly.

The actual use, please refer to FIG. 1 to FIG. 6 again. The technical analysis host 30 is wirelessly connected to the acceleration sensor 11 of the launching stand 10, the wireless camera 20, the foot tracking device 40 and the gyro group 50. The launching stand 10 is set at the starting line of the track, the wireless cameras 20 are arranged between the 0 m to 100 m on both sides of the track at a distance of 10 m from each other, and the foot tracking devices 40 and the gyro group 50 are mounted on the runner, and the size and weight of the foot tracking devices 40 and the gyro group 50 do not affect the runner's performance. Therefore, this system is easy to set up and haves the advantage of low construction cost. Since the starting cue is not exactly the same time point as the runner actually starts because each runner has different instant response, if the cue time is used as the starting time for curve analysis, there will be data distortion problems. Therefore, the acceleration sensor 11 is installed on the back of the pedal 13, when the runner steps onto the pedal 13, the launching stand 10 generates a synchronous displacement to collect an accurate starting time of the runner. At the same time, the technical analysis host 30 synchronically actives all of the wireless cameras 20 so that all collected images and data can be based on the same time axis. When the runner passes by the wireless camera 20, the instantaneous speed is obtained through photography, and then the technical analysis host 30 generates the 100 m speed curve L1 (speed-distance curve graph). The 100 m speed curve L1 usually has the continuous reduced acceleration section L2 formed on the 100 m speed curve L1 because the speed in the starting action phase fails to smoothly connect to the speed in the acceleration phase, which is a common occurrence that the running speed of the runner suddenly drops and then rises. This occurrence may occur between the track 30 m and 80 m and it is not easy to find effective improvements in the conventional training method. This system of the present invention uses the 100 m speed curve L1 to directly identify the continuous reduced acceleration section L2.

Figure 4:
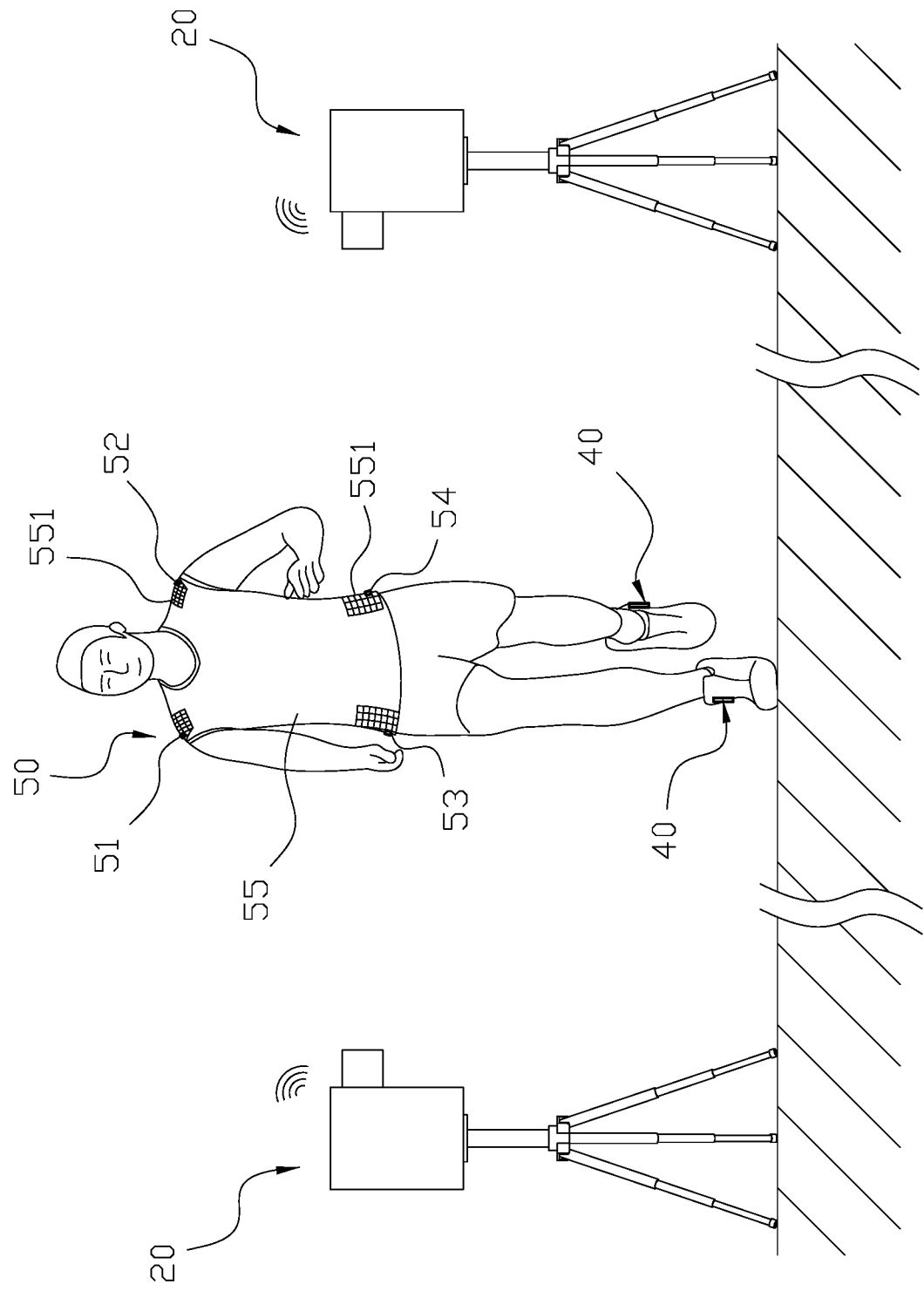
FIG. 4 is a schematic drawing showing the wireless camera on both sides of the track of the preferred embodiment according to the present invention.
Figure 5:
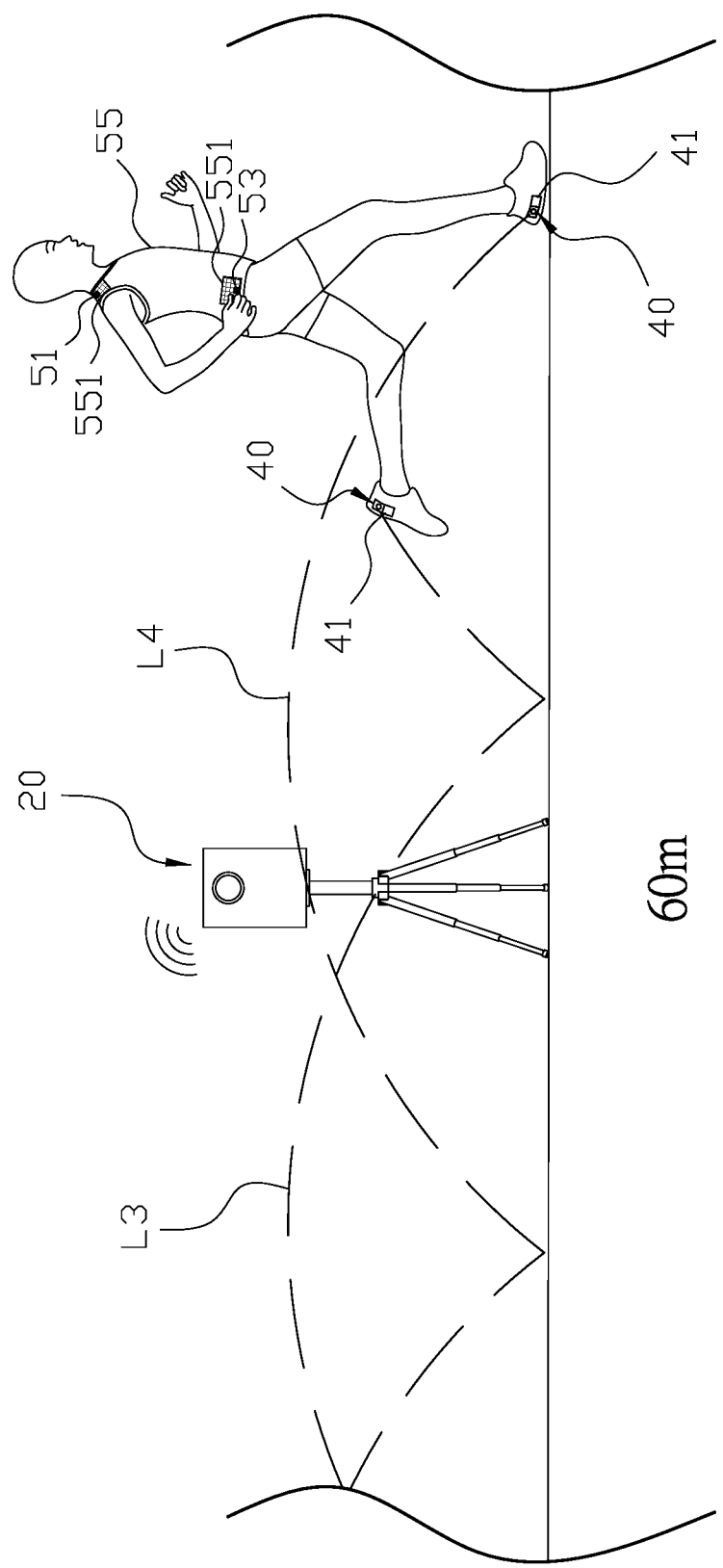
FIG. 5 is a schematic drawing of the foot trajectory curve of the preferred embodiment according to the present invention.
Figure 6:
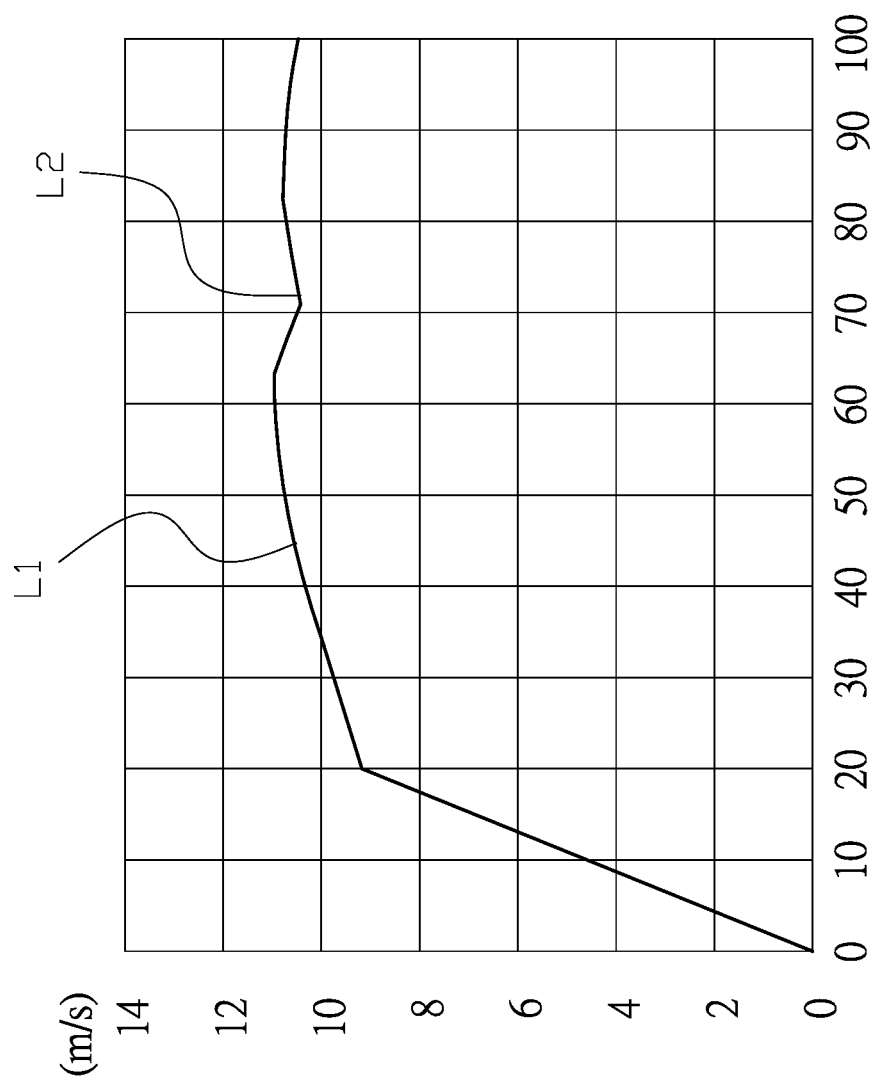
FIG. 6 is a schematic drawing of the 100 m speed curve of the preferred embodiment according to the present invention.

Please refer to FIGS. 1, 4 and 5. The foot tracking devices 40 provide illumination for the wireless cameras 20 at two sides to take the continuous left foot trajectory curve L3 and the continuous right foot trajectory curve L4. When the technical analysis host 30 extracts the continuous left foot trajectory curve L3 and the continuous right foot trajectory curve L4 at the continuous reduced acceleration section L2 and determines according to the timeline whether the continuous left foot trajectory curve L3 and the continuous right foot trajectory curve L4 causing the continuous reduced acceleration section L2. If the left and right foot span changes or the pedaling time changes is the reason of the continuous reduced acceleration section L2, this part can be targeted for training to eliminate the continuous reduced acceleration section L2 of the 100 m speed curve L1, so as to improve the speed consistency of the 100 m track.

Figure 7:
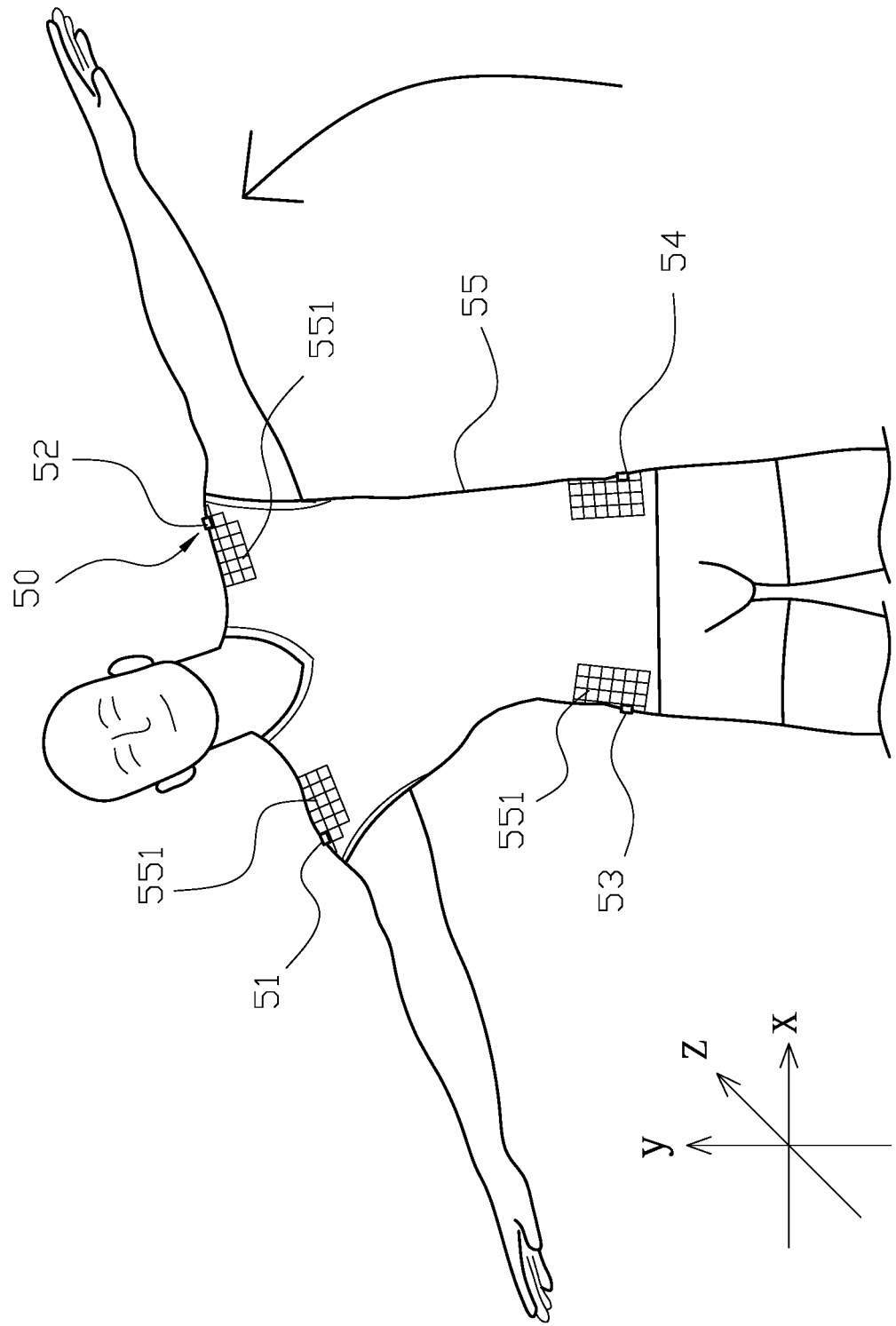
FIG. 7 is a schematic drawing of left and right movements of the torso the runner of the preferred embodiment according to the present invention.
Figure 8:
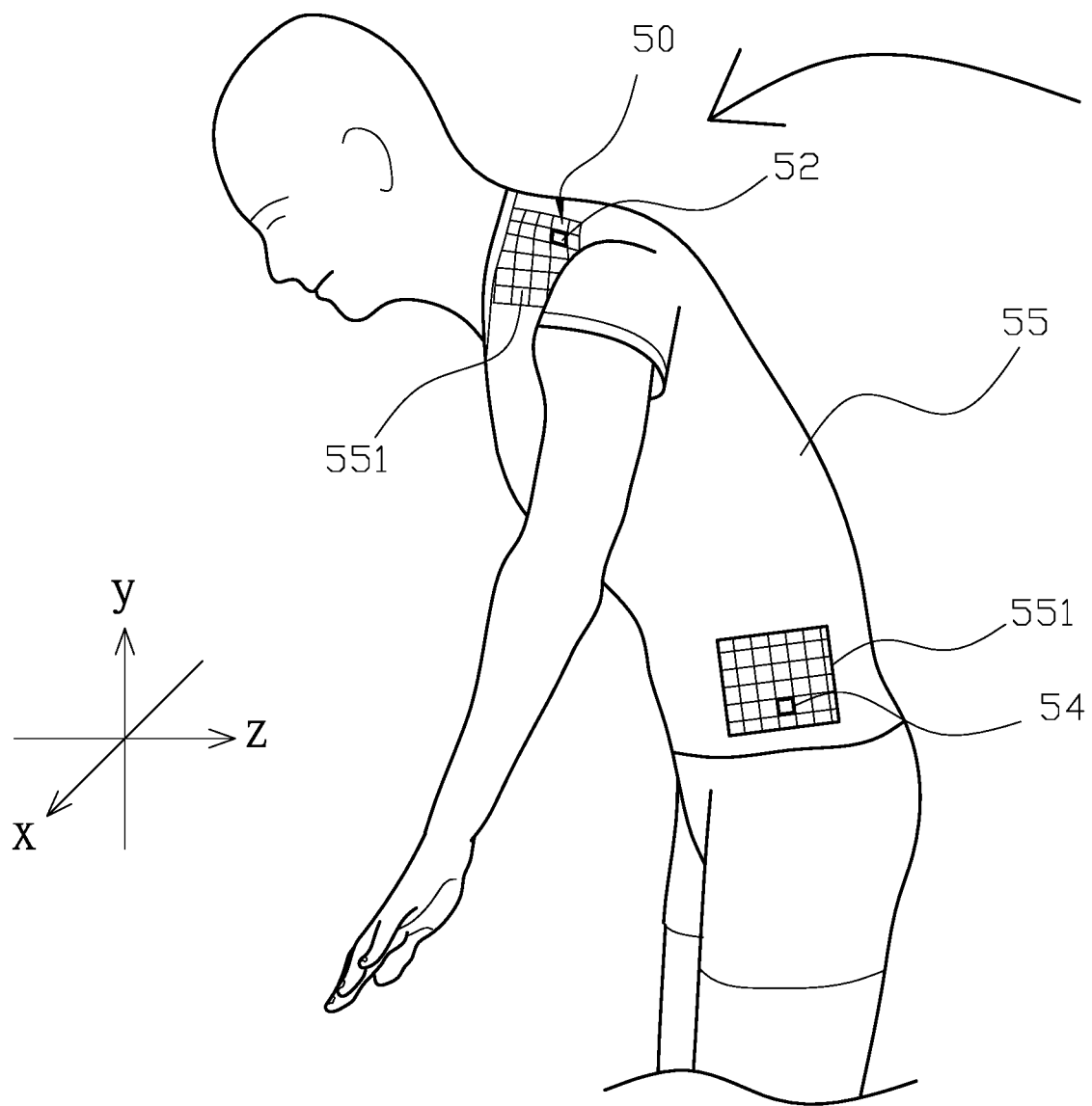
FIG. 8 is another schematic drawing of back and forth movements of the torso the runner of the preferred embodiment according to the present invention.

Furthermore, please refer to FIGS. 7 and 8 with FIG. 1. When the runner is running on the track, the wireless cameras 20 directly take the dynamic images of the runner, and the dynamic images are transferred to the technical analysis host 30 for storage and analysis. Moreover, the gyro group 50 and the wireless cameras 20 can be set synchronously start with the acceleration sensor 11 to correct the timing of the gyro group 50 and the wireless cameras 20, and the gyro group 50 obtain the changes of the X axis, the Y axis and the Z axis of the first gyro 51, the second gyro 52, the third gyro 53 and the fourth gyro 54 through the statistical analysis of the changes of X axis, Y axis and Z axis to obtain the relative oscillations of the runner at each time point. For example, FIG. 7 shows the runner's right shoulder tilting during running, that is, the change in the distance between the X and Z axes of the first gyro 51 and the second gyro 52 is significantly greater than that between the third gyro 53 and the fourth gyro. 54, which indicates the left and right tilt deformation of the runner's upper body. FIG. 8 shows the runner leaning forward during running, that is, the change in the distance between the Y axis and Z axis of the first gyro 51 and the second gyro 52 is obviously greater than that between the third gyro 53 and the fourth gyro 54, and at the same time, the vertical angular velocity of the first gyro 51 and the second gyro 52 also have obvious changes, which indicates the front and back tilt deformation of the runner's upper body. The overall situations such as twisting or rotating of the runner's torso during running can be analyzed through the displacement distances of the X, Y and Z axes between the first gyro 51, the second gyro 52, the third gyro 53 and the fourth gyro 54. To sum up, the amplitude of swing and the amount of distortion are the relative oscillations measured by the gyro group 50 and are used to obtain monitoring data and analysis of the non-rigid human body to learn the core capabilities of the runner. Moreover, the relative oscillations of the gyro group 50 and the continuous reduced acceleration section L2 at each time point are integrated to judge whether the relative oscillations are the main cause of the continuous reduced acceleration section L2, and the factors caused the relative oscillations can be used as the basis for adjusting the runner's running postures, so as to gradually improve runner's bad postures and reduce excess physical exertion. In this way, the main factors of the continuous reduced acceleration section L2 and the modification training method are accurately evaluated. Furthermore, the non-rigid torso movements measured by the gyro group 50 and the foot curve generated by the foot tracking device 40 are combined to analyze and find out the condition prone to wrong postures and imbalance of the center of gravity, by the synchronously incorporating the left foot trajectory curve L3, the he right foot trajectory curve L4 and the relative oscillations allows the runner's torso to be observe in all directions, so that the runner's core capabilities can be monitored and analyzed more comprehensively, thereby providing reasonable running posture correction solutions to effectively overcome the speed reduction problem.

Figure 2:
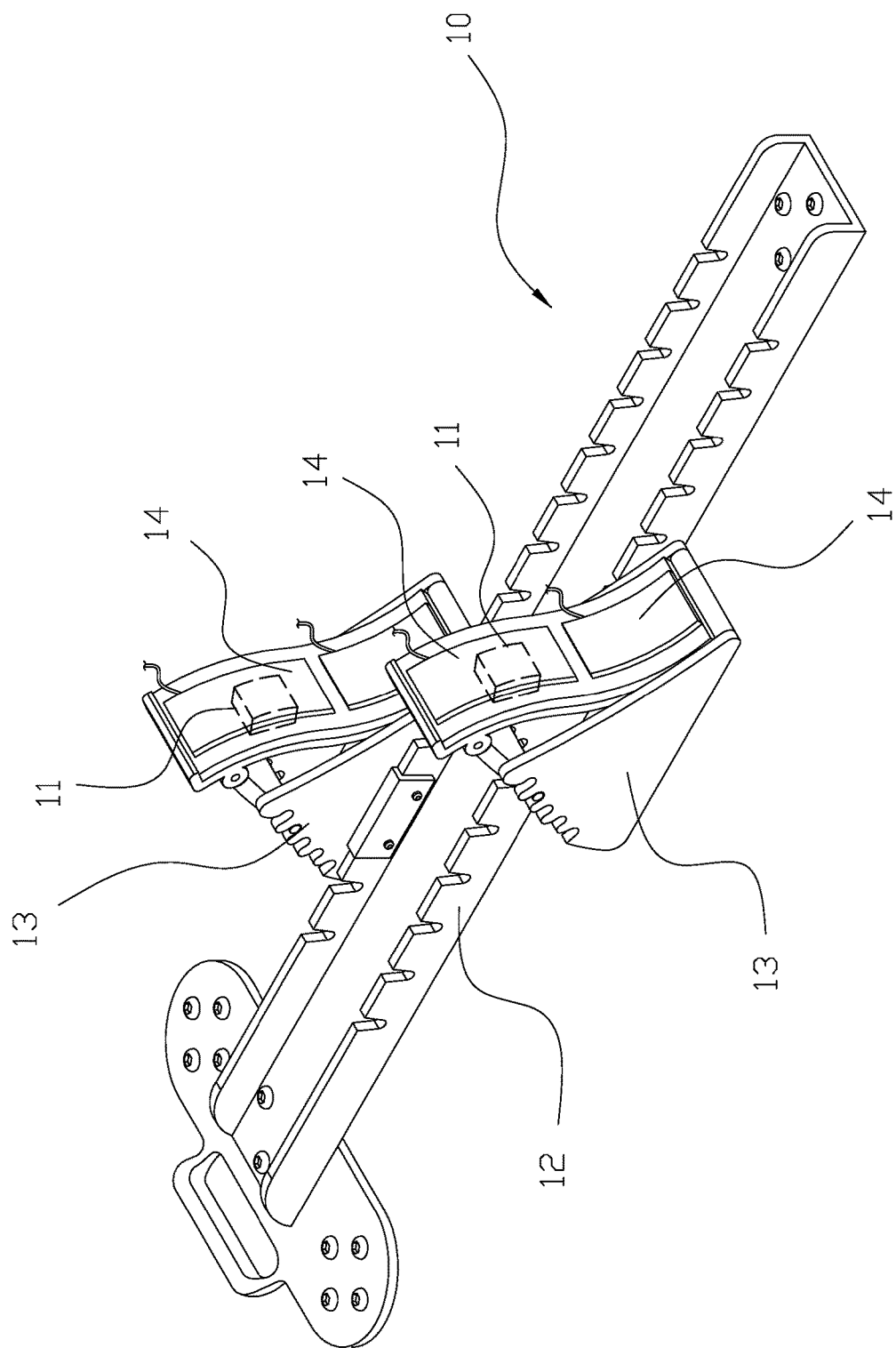
FIG. 2 is a perspective view of the launching stand of the preferred embodiment according to the present invention.
Figure 3:
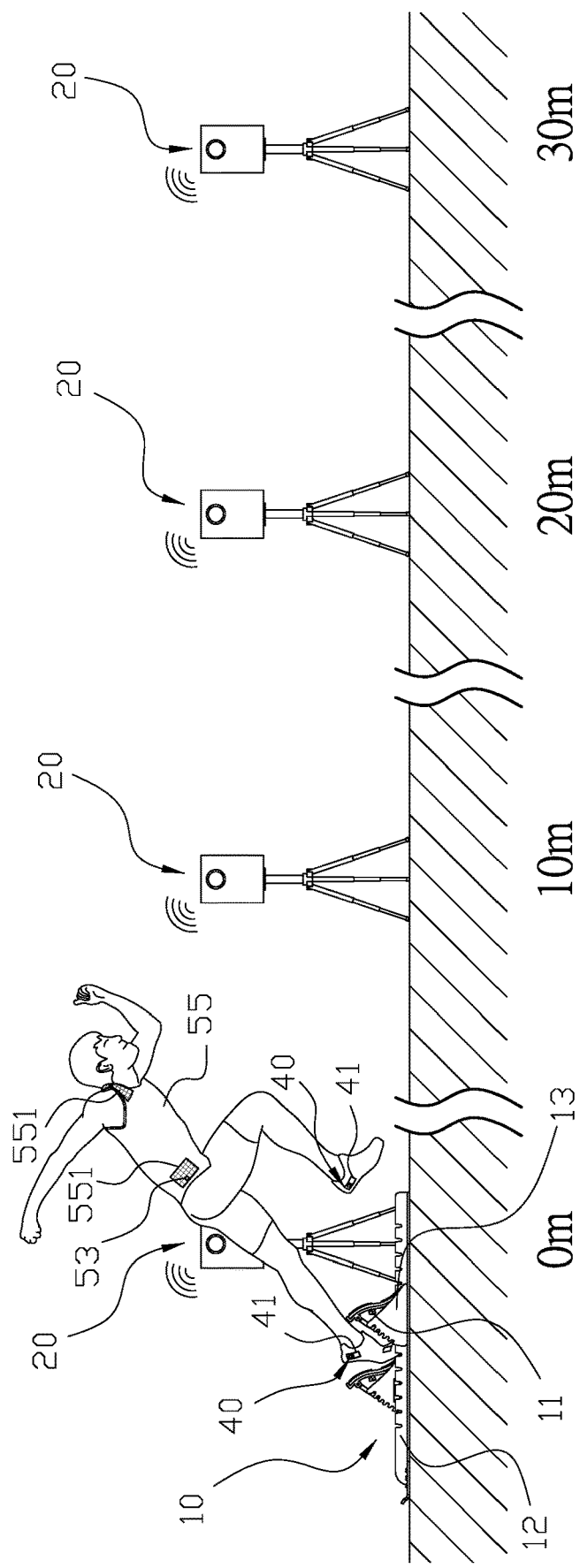
FIG. 3 is a schematic drawing of the starting action of the preferred embodiment according to the present invention.

In addition, please refer to FIGS. 1, 2 and 3. The front of the pedal 13 of the launching stand 10 is equipped with a plurality of the pressure sensors 14, the pressure sensor 14 is connected to the technical analysis host 30, and the pressure sensor 14 collects the foot pressure distribution data and cooperates with the starting moment images taken by the wireless cameras 20 at the launching stand 10. With the foot pressure distribution data and the starting moment images of the runner, the starting actions and the change of the running center of gravity are obtained, to judge whether the runner has a too fast starting speed and causing the problem of unable to connect to the acceleration stage, and then to analyze whether it is the main reason for the continuous reduced acceleration section L2, so as to effectively adjust the proper position of the pedals 13.

To further explain, please observe from the FIGS. 1, 2, and 3. The foot tracking device 40 further has a gravity sensor 41, and the gravity sensor 41 generates the impact signals when the runner's foot steps on the ground. The impact signals are transmitted wirelessly to the technical analysis host 30, and then the time point of the moment when the foot steps on the ground is accurately obtained, so as to modify the left foot trajectory curve L3 and the right foot trajectory curve L4 to integrate the data The relative position of at the same time frame more accurately.

To further explain, please observe from the FIGS. 1, 2, and 3. The technical analysis host 30 is capable of inputting the physical characteristics and training data of the runner, and the improvement history of the physical characteristics, training data and the 100 m speed curve L1 is sent to a cloud database 31 via technical analysis host 30. Additional, the physical characteristics of the runner includes gender, length of each limb, height, weight, age, training age, best performance and preferred feet . . . etc. The cloud database 31 uses utilizes an artificial intelligence (AI) algorithm with Internet of Things (IoT) technology to collect and analyze a history of physical characteristics, training data and the 100 m speed curve of each runner to generate a best decision model, which can be provided to a new runner. Through data comparison, the new runner can query and obtain the best decision model with high similarity, so that the new runner can start training with the best decision model from the beginning to improve the speed connection problem. In real practice, the technical analysis host 30 may be a laptop computer connected to the cloud database 31 through a wireless network, and can also be connected to a smart phone or tablet computer, so that the coach can watch the relevant information data changes instantly.

Figure 9:
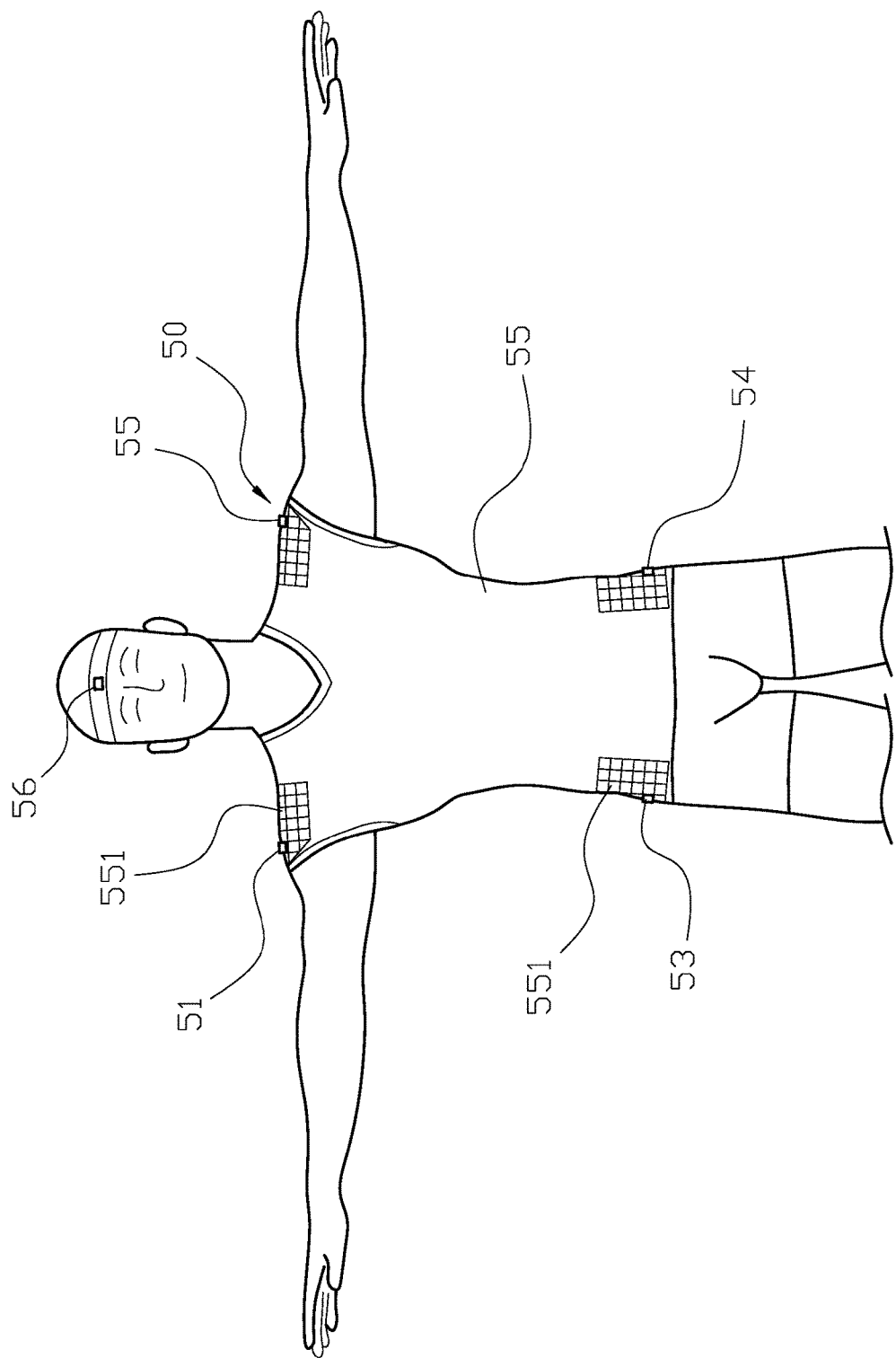
FIG. 9 is a schematic drawing of the fifth gyro of the preferred embodiment according to the present invention.

For further explanation, please refer to FIG. 9. The gyro group 50 is fixed on a tank top 55 for the runner, and the tank top 55 respectively has a coordinate grid 551 at the left shoulder top position, right shoulder top position, the left waist side position and the right waist side position, and the runner's body size can be directly obtained by obtaining the positions of the first gyro 51, the second gyro 52, the third gyro 53 and the fourth gyro 54 on the coordinate grid 551, which helps to quickly set up and ensure that each measurement is set in the same position, thereby improving measurement stability and consistency. Moreover, the first gyro 51, the second gyro 52, the third gyro 53, the fourth gyro 54 are mounted on the tank top 55 with Velcro patches, In addition, the gyro group 50 also includes a fifth gyro 56 mounted on the forehead of the runner, and the Relative position of the head and body of the runner are mediated with the relative oscillations of the fifth gyro 56 on the X, Y and Z axes.

Although the present invention has been explained in relation to its preferred embodiment, it is to be understood that many other possible modifications and variations can be made without departing from the spirit and scope of invention as hereinafter claimed.

What is claimed is:

1. A system for analyzing starts and acceleration phases in squat-style track and field events comprising:
   a launching stand having at least one acceleration sensor and disposed at a starting line of a track;
   a plurality of wireless cameras disposed on two sides of the track between 0 m to 100 m from the starting line and separated from each other by a predetermined distance;
   a technical analysis host connected to the acceleration sensor and the wireless cameras, the acceleration sensor activating the wireless cameras at launch, the wireless cameras collecting instantaneous speed data of a runner at points separated by the predetermined distance, the technical analysis host generating a 100 m speed curve of the runner, and the 100 m speed curve including a continuous reduced acceleration section due to an acceleration phase of the starting action;
   two foot tracking devices installed on two feet of each runner, each foot tracking device providing illumination for the wireless cameras to take a continuous left foot trajectory curve and a continuous right foot trajectory curve; and
   a gyro group for each runner having a first gyro, a second gyro, a third gyro and a fourth gyro, the first gyro mounted on a right shoulder of the runner, the second gyro mounted on a left shoulder of the runner, the third gyro mounted on a right waist of the runner, and the fourth gyro mounted on a left waist of the runner; each gyro group connected to the technical analysis host and measuring relative running oscillations of each runner among an X axis, a Y axis, and a Z axis;
   wherein the technical analysis host determines whether to generate the continuous reduced acceleration section of a runner according to the left foot trajectory curve and the right foot trajectory curve or according to relative oscillation of the body of the runner.

2. The system for analyzing starts and acceleration phases in squat-style track and field events as claimed in claim 1, wherein the launching stand has an adjusting support connected to two pedals, and each pedal is able to move along the adjusting support, and the acceleration sensor is installed behind the pedals.

3. The system for analyzing starts and acceleration phases in squat-style track and field events as claimed in claim 2, wherein a plurality of pressure sensors are installed at a front side of each pedal, the pressure sensors are electrically connected to the technical analysis host, and the technical analysis host determines whether to generate the continuous reduced acceleration section according to foot pressure distribution collected by the pressure sensors and starting moment images captured by the wireless cameras at the launching stand.

4. The system for analyzing starts and acceleration phases in squat-style track and field events as claimed in claim 1, wherein physical characteristics and training data of each runner can be input into the technical analysis host and sent to a cloud database through the technical analysis host.

5. The system for analyzing starts and acceleration phases in squat-style track and field events as claimed in claim 4, wherein the cloud database utilizes an artificial intelligence (AI) algorithm with Internet of Things (IoT) technology to collect and analyze a history of physical characteristics, training data and the 100 m speed curve of each runner to generate a best decision model, which can be provided to a new runner.

6. The system for analyzing starts and acceleration phases in squat-style track and field events as claimed in claim 1, wherein each gyro group further comprises a fifth gyro mounted on a forehead of the runner, and the technical analysis host determines relative positions of each runner's head and forehead according to relative oscillations along the X axis, the Y axis, and the Z axis collected by the fifth gyro.

7. The system for analyzing starts and acceleration phases in squat-style track and field events as claimed in claim 1, wherein each gyro group is mounted on a tank top worn by the runner, the tank top has a plurality of coordination grids respectively disposed on the left shoulder, the right shoulder, the left waist, and the right waist, with coordination of the first gyro, the second gyro, the third gyro and the fourth gyro to obtain physical dimensions of the runner.

8. The system for analyzing starts and acceleration phases in squat-style track and field events as claimed in claim 7, wherein the first gyro, the second gyro, the third gyro, and the fourth gyro are secured onto the tank top with hook and loop fastener.

9. The system for analyzing starts and acceleration phases in squat-style track and field events as claimed in claim 1, wherein the foot tracking device further has a gravity sensor, the gravity sensor generates impact signals when a foot of the runner makes contact with ground, and the impact signals are sent wirelessly to the technical analysis host for modifying the left foot trajectory curve and the right foot trajectory curve.

\* \* \* \* \*